United States Patent
Frey, II et al.

(10) Patent No.: US 9,351,927 B2
(45) Date of Patent: *May 31, 2016

(54) PHARMACEUTICAL COMPOSITIONS FOR TREATMENT OF PATIENTS WITH NEURODEGENERATION FOLLOWING ISCHEMIC INSULT

(75) Inventors: William H. Frey, II, White Bear Lake, MN (US); Samuel Scott Panter, San Francisco, CA (US); Leah Ranae Bresin Hanson, Vadnais Heights, MN (US); Annina Roeytenberg, San Francisco, CA (US)

(73) Assignee: HealthPartners Researh Foundation, Bloomington, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/829,844

(22) Filed: Jul. 2, 2010

(65) Prior Publication Data

US 2010/0267834 A1 Oct. 21, 2010

Related U.S. Application Data

(63) Continuation of application No. 11/580,366, filed on Oct. 13, 2006, now Pat. No. 7,776,312, which is a continuation-in-part of application No. 11/200,898, filed on Aug. 10, 2005, now Pat. No. 7,618,615, application No. 12/829,844, which is a continuation of application No. 12/619,009, filed on Nov. 16, 2009, now Pat. No. 8,568,691.

(60) Provisional application No. 60/601,547, filed on Aug. 13, 2004.

(51) Int. Cl.
| | |
|---|---|
| *A61K 9/00* | (2006.01) |
| *A61K 31/165* | (2006.01) |
| *A61K 38/16* | (2006.01) |
| *A61K 38/28* | (2006.01) |
| *A61K 31/195* | (2006.01) |
| *A61K 38/18* | (2006.01) |
| *A61K 38/20* | (2006.01) |
| *A61K 38/30* | (2006.01) |
| *A61K 45/06* | (2006.01) |

(52) U.S. Cl.
CPC .............. *A61K 9/0043* (2013.01); *A61K 31/165* (2013.01); *A61K 31/195* (2013.01); *A61K 38/1841* (2013.01); *A61K 38/2006* (2013.01); *A61K 38/28* (2013.01); *A61K 38/30* (2013.01); *A61K 45/06* (2013.01); *A61K 2800/522* (2013.01)

(58) Field of Classification Search
None
See application file for complete search history.

(56) References Cited

U.S. PATENT DOCUMENTS

| | | | |
|---|---|---|---|
| 5,624,898 A * | 4/1997 | Frey, II | 514/8.4 |
| 5,849,290 A | 12/1998 | Brown et al. | |
| 6,313,093 B1 | 11/2001 | Frey, II | |
| 2003/0072793 A1 | 4/2003 | Frey, II et al. | |
| 2004/0101521 A1 | 5/2004 | Andersen | |
| 2004/0167217 A1 | 8/2004 | Scapagnini et al. | |

FOREIGN PATENT DOCUMENTS

WO WO91/07947 6/1991

OTHER PUBLICATIONS

Atkins et al., Neurology International, 2(E1): 1-3, published Apr. 6, 2011.*
Youdim et al., Ann NY Acad Sci, 1012:306-325, Mar. 2004.*
Lan and Jiang, J Neural Transmission, 104:469-481, 1997.*
The Merck Index, Published by Merck & Co., Inc., Whitehouse Station, NJ (1996).*
Wishart et al., J. Nucleic Acids Res., 34(Database issue):D668-72, published Jan. 1, 2006. Retrieved online at <http://www.drugbank.ca/drugs/DB00746> Retrieved on Sep. 2, 2011.*
Novartis prescribing information sheet for Desferal dated Oct. 2002. Online. Retreieved from <http://web.archive.org/web/20050519023024/http://www.pharma.us.novartis.com/product/pi/pdf/desferal.pdf>. Retrieved on Aug. 1, 2012.*
Reger et al., Neurobiology of Aging, 27:451-458, 2006.*
Fawcett et al., Brain Research, 950:10-20, 2002.*
Metals in our minds: therapeutic implications for neurodegenerative disorders, P. Murali Doraiswamy and Anne E. Finefrock, The Lancet Neurology vol. 3, Jul. 2004 (pp. 431-434).
Delivery of Insulin-Like Growth Factor-I to the Rate Brain and Spinal Cord Along Olfactory and Tridgeminal Pathways Following Intranasal Administration, R.G. Thorne, et al., Neuroscience 127 (2004) (pp. 481-496).
Maxwell and Salniknow, Cancer Biology and Therapy 3(1): 29-35. (Jan. 2004).
Brenneisen et al., The Journal of Biological Chemistry 273(9): 5279-5287. (Feb. 27, 1998).
Crapper McLachlan et al., Lancet 337(8753): 1304-1308. (Jun. 1, 1991).

(Continued)

*Primary Examiner* — Daniel E Kolker
*Assistant Examiner* — Stacey N MacFarlane
(74) *Attorney, Agent, or Firm* — Barnes & Thornburg LLP

(57) ABSTRACT

Pharmaceutical compositions for treating and/or pre-treating or preconditioning the animal central nervous system against the effects of Alzheimer's Disease including the associated neurodegeneration and cognitive, behavioral and physical impairments. In one embodiment, an effective dose of deferoxamine (DFO) is administered to the upper one-third of the subject patient's nasal cavity to effectively bypass the blood-brain barrier, thereby allowing application of the DFO dose directly to the central nervous system.

8 Claims, 13 Drawing Sheets

(56) References Cited

OTHER PUBLICATIONS

Chaston and Richardson, American Journal of Hematology 73: 200-210. (2003).
King RG, Med J Aust, 142(6; 352, Mar. 18, 1985).
Kruck et al., Clin Pharmacol Ther, 48(4): 439-446, Oct. 1990.
Gordon et al., Amer J Med Sci, 297(5): 280-284, May 1989.
Wang and Semenza, Blood, 82(12): 3610-3615, Dec. 15, 1993.
Kamat et al., J. Alzheimer's Dis., 15(3): 473-493, Nov. 2008.
(Abstract cited) A. Smith. Links between cell-surface events involving redox-active copper and gene regulation in the hemopexin heme transport system. Antioxidants and Redox Signaling 2(2): 157-175. (2000).
Hanson et al: "Intranasal Deferoxamine Provides Increased Brain Exposure and Significant Protection in Rat Ischemic Stroke", The Journal of Pharmacology and Experimental Therapeutics, Sep. 2009; 330(3), pp. 679-686.
House et al: "Aluminum, iron, zinc and copper influence the in vitro formation of amyloid fibrils of abeta42 in a manner which may hae consequences for metal chelation therapy in Alzheimer's disease", J Alzheimers Dis. Jun. 2004; 6(3) 291-301.
Yokel et al: "Entry, Half-Life, and Desferrioxamine-Accelerated Clearance of Brain Aluminum", Toxicol Sci. Nov. 2001;64(1):77-82.

* cited by examiner

PHARMACEUTICAL COMPOSITIONS FOR TREATMENT OF PATIENTS WITH NEURODEGENERATION FOLLOWING ISCHEMIC INSULT

CROSS-REFERENCE TO RELATED APPLICATIONS

This is a continuation-in-part of U.S. patent application Ser. No. 11/200,898 filed Aug. 10, 2005, which claims the benefit and priority of U.S. provisional patent application Ser. No. 60/601,547 filed Aug. 13, 2004.

INVENTORS

William H. Frey II, a citizen of the United States, residing in White Bear Lake, Minn.
Samuel Scott Panter, a citizen of the United States, residing in San Francisco, Calif.
Leah Ranae Bresin Hanson, a citizen of the United States, residing in Vadnais Heights, Minn.
Annina Roeytenberg, a citizen of Israel and of France, residing in San Francisco, Calif.

BACKGROUND OF THE INVENTION

1. Field of the Invention

The present invention is directed to methods and pharmaceutical compositions for differentially reducing, inhibiting or preventing the increase in gene expression caused by neurological disorders to precondition, treat and/or provide neuroprotection to the animal central nervous system against ischemia, neurodegeneration, metal poisoning and trauma, including associated cognitive, behavioral and physical impairments.

2. Description of the Related Art

Certain medical procedures, for example coronary artery bypass graft (CABG) surgery, are associated with neurological complications. In the case of CABG, the surgery is performed on more than 800,000 patients worldwide each year. Many of the CABG procedures performed are associated with neurological complications. These complications range from stroke in up to 16% of the patients to general cognitive decline with 50% of patients having impairment post-surgery and with progressive decline occurring in some patients over the next five years. In addition, physical and behavioral impairment manifest in some CABG patients. Newman M F et al., N. Eng. J. Med. 344:395-402 (2001); Brillman J., Neurol. Clin. 11:475-495 (1993); and Seines, O. A., Ann. Thorac. Surg. 67:1669-1676 (1999) are instructive.

Originally, it was hypothesized that the neurological complications associated with CABG surgery were either procedure or patient-related. The procedure generally implicated as potentially harmful was cardiopulmonary bypass using a pump and oxygenator. However, a recent study reports no difference in cognitive outcome between groups of patients undergoing CABG surgery performed with, or without, the pump and oxygenator. Such results suggest that the neurological impairments following CABG surgery may, in fact, be patient-related and, as a result, amenable to therapeutic manipulation.

In addition, patients at risk for, or diagnosed with disorders involving neurological impairments, e.g., Alzheimer's disease, Parkinson's disease, stroke, traumatic brain injury, spinal cord injury may benefit from similar therapeutic manipulation. See Crapper McLachlan, D. R., Dalton, A. J., Kruck, T. P. A., Bell, M. Y., Smith, W. L., Kalow, W., and Andrews, D. F. Intramuscular desferrioxamine in patients with Alzheimer's disease. The Lancet 337:1304-1308, 1991.

A number of neurodegenerative disorders are known to have metal-associated pathology, i.e., resulting at least in part from metal poisoning, and may benefit from the therapeutic manipulation contemplated by embodiments of the present invention. These include AD, PD, Creutzfeldt-Jakob disease, familial amyotrophic lateral sclerosis, lewy-body dementia, carotid atherosclerosis, tardive dyskinesia, multiple sclerosis, Wilson's disease, progressive supranuclear palsy, Hallervorden-Spatz syndrome, multisystem atrophy, Huntington's disease, familial basal ganglia degeneration, Down's syndrome, cataracts, haemochromatosis, cerebral haemorrhage and head injury. See P. M. Doraiswamy and A. E. Finefrock, Metals in our minds: therapeutic implications for neurodegenerative disorders, The Lancet Neurology, Vol. 3, July 2004.

In general, ischemic conditions activate a number of genes that are important in the cellular and tissue adaptation to low oxygen conditions. These genes include erythropoietin, glucose transporters, glycolytic enzymes, and the vascular endothelial growth factor (VEGF). VEGF is a major angiogenic factor that has been shown to activate new blood vessel formation. Transcriptional up-regulation has been shown to be implicated in the induction of the VEGF gene, an action mediated by the specific binding of the hypoxia-inducible factor-1 (HIF-1) to the hypoxic response element (HRE).

In addition, caspase molecules, e.g., those involved in cytokine maturation (caspase-1, -4 and -5) and those involved in cellular apoptosis (caspase-2, -3, -4, -6, -7, -8, -9, -10 and -12), mediate essential key proteolytic events in inflammatory cascades and the apoptotic cell death pathway. Caspase-12 has been shown to be a mediator of apoptosis induced by endoplasmic reticulum stress including amyloid-beta toxicity, suggesting that, inter alia, caspase-12 may contribute to the pathogenesis of Alzheimer's disease. See, e.g., Saleh M Vaillancourt J P, et al., *Differential Modulation of Endotoxin Responsiveness by Human Caspase-12 Polymorphisms*, Nature, 2004 May 6; 429 (6987):75-9. In addition, caspases, e.g., caspace-4 and caspase-12, are present in elevated concentrations following stroke. Therefore, a therapeutic treatment that inhibits, reduces or prevents cell death and inflammation, resulting, in turn, inhibits, reduces or prevents the expression of genes for caspases would be helpful in preventing and/or minimizing certain effects of, inter alia, stroke and/or Alzheimer's disease, as well as in pretreating these conditions to minimize the effects of such disorders.

It is further known that expression of the gene for the matrix metallopeptidase-9 (MMP9) is increased during and after a stroke. MMP9 is involved in apoptosis and has been linked to an increased risk for hemorrhagic transformation following ischemic episodes such as stroke. In addition, MMP9 has been linked to increased brain swelling (inflammation) and cellular damage after a stroke. Therefore, a therapeutic treatment that inhibits, reduces or prevents cell death and inflammation and, in turn, reducing, inhibiting or preventing the expression of genes for MMP9 would be helpful in preventing and/or minimizing certain effects of, inter alia, stroke and/or Alzheimer's disease, as well as in pretreating to minimize the effects of such disorders.

Expression of the gene for annexin-A1 is increased during and after stroke or ischemic episode. It is known that expression of annexin-A1 increases in response to inflammation, therefore, a therapeutic treatment that inhibits, reduces or prevents inflammation, e.g, brain inflammation, resuling in the inhibition, reduction or prevention of expression of the gene for annexin-A1, may be helpful in preventing certain effects of, inter alia, stroke, as well as in pretreating to minimize the effects of such disorders.

The gene for heme oxygenase (decycling)-1 is known to increase expression during and after stroke and in response to oxidative stress in stroke and other central nervous system disorders such as Alzheimer's disease. Therefore, a therapeutic treatment that inhibits, reduces or prevents oxidative stress as evidenced by the inhibited, reduced or prevented expression of heme oxygenase (decycling)-1, may be helpful in preventing certain effects of, inter alia, stroke, as well as in pretreating to minimize the effects of such disorders.

Expression of the gene for insulin-like grown factor-2 (IGF-2) is increased during and following stroke. IGF-2, administered intracerebroventricularly following hypoxia/ischemia has been shown to cause neurodegenerative effects, including inter alia, an increase neuronal loss in the hippocampus and dentate gyrus. Moreover, IGF-2 has been shown to block the neuroprotective effects of IGF-1. Therefore, a therapeutic treatment that inhibits, prevents or reduces these neurodegenerative effects, as evidenced by the reduced expression of IGF-2, may be helpful in inhibiting, reducing or preventing certain effects of, inter alia, stroke, Alzheimer's disease and other central nervous system disorders, as well as in pretreating to minimize the effects of such disorders.

The HIF-1 transcription factor is a heterodimer composed of HIF-1α and HIF-1β and regulates the adaptive response to hypoxia in animal cells. HIF-1α accumulates under hypoxic conditions, but is virtually undetectable in normal oxygen conditions. HIF-1β, on the other hand, is readily found in all cells. The HIF-1 heterodimer is believed to be neuroprotective against ischemia through the activation of EPO and VEGF.

HIF-1α has been shown in vitro to be activated by metal chelators, including both iron and copper chelating agents. A particular example of such an agent is deferoxamine (DFO), a hexadentate iron chelator, with kinetics similar to those associated with hypoxia, resulting in increased expression of HIF-1 target genes, including EPO and VEGF. Other examples of iron chelators are deferasirox and deferiprone. DFO is also known to stabilize HIF-1 subunits, possibly by chelating and inactivating the iron that plays a role in targeting the subunit for proeolytic degradation under normoxic conditions.

In vivo studies have demonstrated that DFO induces HIF-1α in neonatal and adult rats, injecting the chelator either subcutaneously (s.c.) or intraperitoneally (i.p.), typically in very high dosage. In addition, studies indicate that the following substances stimulate and/or stabilize HIF-1α: insulin, IGF-I, heregulin insulin, heregulin, TGFbeta, IL-1 beta, TNFalpha, cobalt, pyruvate, oxalacetate and lactate.

Problems exist, however, with the administration of DFO intravenously. DFO is not generally injected intravenously for at least two reasons. First, it is a small molecule and, as a result, is eliminated rapidly through the kidney. The typical plasma half-life in humans is less than 10 minutes. Second, the injection of an intravenous bolus of DFO causes acute hypotension that is rapid, may lead to shock and may be lethal. These characteristics have limited the utility of DFO in particular as a neuroprotective agent.

One published study administered DFO intranasally to iron overloaded patients. G. S. Gordon et al., Intranasal Administration of Deferoxamine to Iron Overloaded Patients, (1989) Am. J. Med. Sci. 297(5):280-284. In this particular study, DFO was administered to the patients as a nasal spray in a volume of 75 microliters per spray. Significantly, such sprays are known to deposit the drug or other substance in the lower third of the nasal cavity. This is verified by patient observations stating that a bad taste in the mouth was resulting from the drug passing through the nasopharynx and into the mouth. As a result, this study did not involve delivering the drug to the upper third of the nasal cavity. Thus, the drug would not have reached the olfactory epithelium or the olfactory nerves. As a result, delivery of the drug to the CNS would be less than optimal.

It is recognized that intranasal delivery to the CNS may occur along both the olfactory and trigeminal nerve pathways. See Thorne, R G (2004), Delivery of Insulin-Like Growth Factor-I to the Rat Brain and Spinal Cord Along Olfactory and Trigeminal Pathways Following Intranasal Administration, Neuroscience, Vol. 127, pp. 481-496. Optimal delivery taking advantage of both pathways is accomplished by administering the substance in the upper third of the nasal cavity.

Regarding Alzheimer's disease, some studies indicate that cerebral vascular problems occur first, followed by neurodegeneration in later stages of the disease. For example, see The Lancet Neurology, vol. 3, page 184-190, Jack C. de la Torre (March, 2004). Thus, it may be possible to prevent, mitigate or treat the effects of Alzheimer's disease at the appropriate disease stage through therapeutic manipulation targeted toward mitigation or prevention of cerebral ischemia or neurodegeneration.

In a published patent application, U.S. Pat. App. No. 20020028786 by William H. Frey II (also a co-inventor of the present application) entitled METHODS AND COMPOSITIONS FOR ENHANCING CELLULAR FUNCTION THROUGH PROTECTION OF TISSUE COMPONENTS, various substances are discussed that may be administered intranasally to treat various diseases and conditions. The entire contents of this reference are hereby incorporated by reference.

BRIEF SUMMARY OF THE INVENTION

Given the situation described above there is a need for a method for efficiently and safely conditioning, or preconditioning, the animal CNS to prevent or minimize cognitive, behavioral and physical impairment due to ischemia, neurodegeneration, CNS trauma and free radical damage from copper, zinc and iron. In addition, there is a need for a method for efficiently and safely conditioning and treating the animal CNS to treat existing cognitive, behavioral and physical impairment due to ischemia, neurodegeneration, CNS trauma and free radical damage from copper and iron. Further, there is a need to optimize the administration or delivery of a therapeutic agent.

Methods and pharmaceutical compositions for preconditioning the CNS to neuroprotect against, minimize and/or prevent the effects of ischemia and the cognitive, behavioral and physical impairments that often accompany ischemic episodes by stimulating and stabilizing hypoxia-inducible factor-1α (HIF-1α) are provided herein. HIF-1α is known to provide a neuroprotective benefit under ischemic conditions. Patients at risk for certain diseases or disorders that carry a concomitant risk for ischemia may benefit, e.g., those at risk for Alzheimer's disease, Parkinson's disease, Wilson's Disease, Huntington's disease, or stroke. Patients undergoing certain medical procedures that may result in ischemia may also benefit, e.g., coronary artery bypass surgery.

In addition, methods and compounds for treating patients that have undergone an ischemic episode to minimize the effects of the ischemia are provided herein.

Initially, under a representative embodiment of the invention, the possibility of an ischemic episode or neurodegeneration is recognized. Intranasal therapeutic agent is administered to the upper third of the nasal cavity to bypass the blood-brain barrier and access the central nervous system directly to avoid unwanted and potentially damaging side effects. Therapeutic agents include those substances that may interact with iron and/or copper such as iron chelators, copper chelators, and/or antioxidants and free radical scavengers. A particular example of such therapeutic agents is the iron chelator deferoxamine (DFO). Another particular example of such a therapeutic agent is the iron chelator deferasirox, marketed as Exjade® by Novartis AG for use in patients with iron overload condition. Still another example of such a therapeutic agent is the iron chelator deferiprone, marketed under the name Ferriprox® by Hind Wing Co., Ltd, Hong Kong specifically for Cooley's Anemia, also known as thalassemia. Presently, both deferasirox and deferiprone are administered orally which, as discussed further herein, has disadvantages over the intranasal delivery methods of the present invention. DFO, deferiprone and deferasirox may also chelate copper as well as other metals. Intranasal administration of DFO is known to stimulate and/or stabilize HIF-1α and provides an efficient and safe method for pre-conditioning the CNS to protect against cerebral ischemia. The effects of pretreating a patient, who ultimately experiences ischemia, include significant reduction of infarct volume following stroke.

Another embodiment of the invention provides a method and pharmaceutical compositions for treating a patient that has undergone an ischemic episode by administering at least one does of a therapeutic agent via intranasal delivery to the upper one-third of the nasal cavity. As discussed above in connection with pretreatment, metal chelators, e.g., DFO, deferasirox or deferiprone, may be used to treat a patient post-stroke. The effects of post-stroke intranasal administration of such a therapeutic agent include significant reduction of infarct volume.

Thus, one embodiment of the invention relates to a method and pharmaceutical compositions for preventing, minimizing and/or treating neurologic complications due to cerebral ischemia as a result of certain medical procedures. The method comprises administering at least one dose of a therapeutic agent via intranasal delivery to the upper one-third of the nasal cavity prior to undergoing a medical procedure that may result in neurologic complications.

Another embodiment of the invention relates to a method and pharmaceutical compositions for preventing, minimizing and/or treating neurologic complications due to cerebral ischemia or neural degeneration as a result of certain medical procedures. The method comprises administering at least one dose of at least one therapeutic agent via intranasal delivery to the upper one-third of the nasal cavity during, prior to and/or after undergoing a medical procedure that may result in neurologic complications. The particular therapeutic agent(s) selected may preferentially chelate iron or copper or a combination of the iron and copper, or otherwise interact with select metals or prevent oxidation/reduction cycling of iron or copper.

Another embodiment of the invention relates to a method and pharmaceutical compositions for preventing, minimizing and/or treating neurologic complications, including protecting against memory loss and improving memory loss, due to cerebral ischemia and/or neurodegeneration for patients at risk for, or diagnosed with, certain medical conditions such as Alzheimer's disease, Parkinson's disease, Creutzfeldt-Jakob disease, familial amyotrophic lateral sclerosis, lewy-body dementia, carotid atherosclerosis, tardive dyskinesia, multiple sclerosis, Wilson's disease, progressive supranuclear palsy, Hallervorden-Spatz syndrome, multisystem atrophy, Huntington's disease, familial basal ganglia degeneration, Down's syndrome, cataracts, haemochromatosis, thalassemia, cerebral hemorrhage, subarachnoic hemorrhage, head injury, and spinal cord injury.

The figures and the detailed description which follow more particularly exemplify these and other embodiments of the invention.

BRIEF DESCRIPTION OF THE DRAWINGS

The invention may be more completely understood in consideration of the following detailed description of various embodiments of the invention in connection with the accompanying drawings, which are as follows.

DETAILED DESCRIPTION OF THE INVENTION, INCLUDING THE BEST MODE

Figure 1:
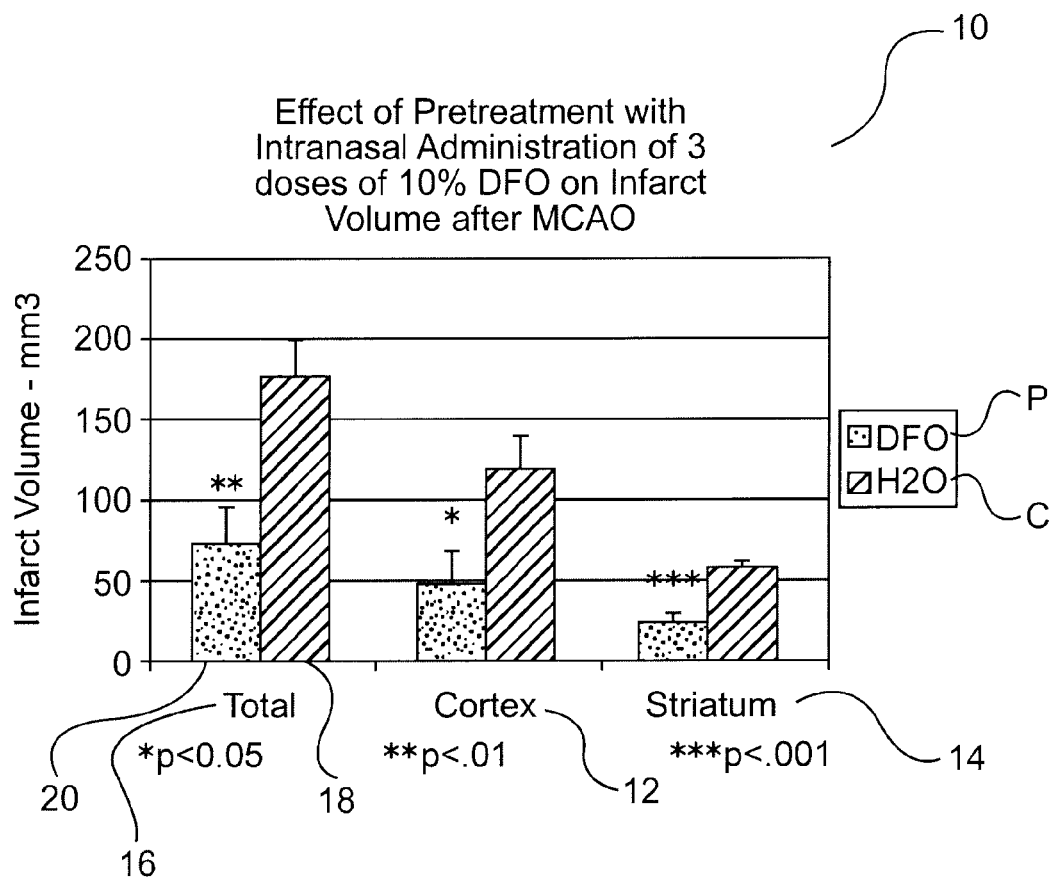
FIG. 1 is a bar graph illustrating pre-stroke treatment with intranasal administration of three doses of 10% DFO and its effect on infarct volume.

While the invention is amenable to various modifications and alternative forms, specifics thereof are shown by way of example in the drawings and described in detail herein. It should be understood, however, that the intention is not to limit the invention to the particular embodiments described.

On the contrary, the intention is to cover all modifications, equivalents, and alternatives falling within the spirit and scope of the invention.

Definitions

As used herein, "central nervous system" (CNS) refers to the brain and spinal cord and associated tissues.

As used herein, "neurological disorder" comprises conditions involving ischemia, i.e., cerebral ischemia, ischemia, stroke, neurodegeneration, neurological complications arising from coronary bypass surgery, Parkinson's disease, Wilson's disease, Huntington's disease, amyotrophic lateral sclerosis, Alzheimer's disease, iron and copper toxicity, iron overload in the brain, thalassemia, metal poisoning of the central nervous system, central nervous system oxidative stress, traumatic brain injury, and spinal cord injury.

An "effective amount" of agent is an amount sufficient to prevent, treat, reduce and/or ameliorate the symptoms, neuronal damage and/or underlying causes of any of the referenced disorders or diseases. In some instances, an "effective amount" is sufficient to eliminate the symptoms of those diseases and overcome the disease itself.

In the context of the present invention, the terms "treat" and "therapy" and "therapeutic" and the like refer to alleviate, slow the progression, prophylaxis, attenuation or cure of ischemia, trauma, metal poisoning or neurodegeneration.

"Prevent", as used herein, refers to putting off, delaying, slowing, inhibiting, or otherwise stopping, reducing or ameliorating the onset of ischemia, trauma, metal poisoning or neurodegeneration. It is preferred that a large enough quantity of the agent be applied in non-toxic levels in order to provide an effective level of neuroprotection. The method of the present invention may be used with any animal, such as a mammal or a bird (avian), more preferably a mammal. Poultry are a preferred bird. Exemplary mammals include, but are not limited to rats, mice, cats, dogs, horses, cows, sheep, pigs, and more preferably humans.

Ischemia or ischemic episode or condition is defined herein to comprise an ischemic condition where the brain or parts of the brain do not receive enough blood flow to maintain normal neurologic function. Various conditions can cause ischemia, including but not limited to stroke. Each of the neurologic disorders defined and discussed herein comprise some level of ischemia.

Thus, methods and pharmaceutical compositions are described herein that, inter alia, prevent, and/or treat conditions cause by the increased expression of genes caused by neurological disorders, e.g., cognitive, behavioral and/or physical impairment.

An alternative to potentially lethal and generally ineffective intravenous injection of metal chelators, e.g., DFO, deferasirox or deferiprone, may be accomplished using an alternative non-invasive method to directly target the substance to the brain and thus the central nervous system (CNS). Intranasal delivery allows substances to be rapidly delivered to the central nervous system, even those that do not readily cross the blood-brain barrier by bypassing the blood-brain barrier and directly exposes the CNS to the delivered substance. In this manner, unwanted systemic side effects are reduced if not eliminated.

Since DFO, similar to other metal chelators such as deferasirox and deferiprone, has a strong Fe-III binding constant ($10^{31}$), it is rapidly eliminated from the blood and does not readily cross the blood-brain barrier. Thus, when metal chelator-based therapeutic agents are administered intravenously, orally or even intranasally—but not directly to the upper one-third of the nasal cavity—to target affected tissues within the brain, the therapeutic effect has been heretofore minimal. Delivery of intranasal DFO to the upper one-third of the nasal cavity has been assessed by administering 6 mg DFO bound to 6 µCi of $^{59}$Fe (as $^{59}$FeCl$_3$) to rats under anesthesia. The IN dose in 60 µL was administered as 6 µL drops over twenty minutes. Following delivery, tissues were removed for analysis. Using scintillation counting, labeled ferrioxamine was detected throughout the brain, with high concentrations detected in the olfactory bulbs, anterior olfactory nucleus, hypothalamus, frontal cortex and cervical spinal cord. Even higher ferrioxamine concentrations were observed in the trigeminal nerves and ventral dura. Peripheral tissues with the highest ferrioxamine concentrations included the olfactory epithelium, thyroid and cervical lymph nodes. By contrast, the blood concentrations of ferrioxamine, taken at 5 minute intervals from dosing up to 25 minutes post-dose, are quite low, indicating a minimization of exposure of the therapeutic agent to non-target tissue. The data provided in Table 1 below, thus illustrates that intranasal DFO, the concentrations having been calculated based on an extrapolation of the ferrioxamine concentration, administered to the upper one-third of the nasal cavity, is effectively delivered to the brain and upper spinal cord, with minimal systemic exposure.

TABLE 1

| Intranasal Delivery of DFO (uM in tissues 25 min. after onset of delivery) | | | | | | | | | |
|---|---|---|---|---|---|---|---|---|---|
| uL delivered | 62 | 65 | 60 | 64 | 62 | 62 | 62 | 66 | 61 |
| uCi delivered | 36.55 | 38.40 | 35.45 | 36.77 | 35.28 | 35.30 | 34.72 | 35.80 | 34.31 |
| mg delivered | 6.15 | 6.44 | 5.95 | 6.29 | 6.05 | 6.05 | 6.07 | 6.45 | 6.00 |
| nmol delivered | 9,361.73 | 9,801.65 | 9,063.49 | 9,583.97 | 9,218.26 | 9,207.99 | 9,237.98 | 9,824.75 | 9,128.91 |
| Drug Delivery Time | 21 | 21 | 20 | 20 | 22 | 20 | 20 | 20 | 18 |
| Time of Perfusion | 25 | 25 | 26 | 25 | 26 | 27 | 26 | 26 | 26 |
| Rat weight | 303 | 302 | 264 | 298 | 309 | 336 | 283 | 318 | 315 |
| RAT # | DF09 | DF10 | DF11 | DF13 | DF14 | DF15 | DF18 | DF19 | DF20 |
| Blood Sample 1 (5:00) | 1.2 | 1.6 | 0.6 | 0.7 | 1.5 | 1.1 | 0.8 | 0.3 | 1.8 |
| Blood Sample 2 (10:00) | 1.1 | 2.1 | 1.1 | 1.2 | 1.8 | 1.7 | 1.0 | 0.4 | 1.9 |
| Blood Sample 3 (15:00) | 1.1 | 2.0 | 0.5 | 0.9 | 1.4 | 1.7 | 1.3 | 0.5 | 2.6 |
| Blood Sample 4 (20:00) | 1.1 | 1.8 | 0.3 | 1.1 | 1.6 | 1.5 | 1.1 | 0.4 | 2.9 |
| Blood Sample 5 (25:00) | 1.8 | 1.6 | 1.8 | 1.5 | 2.2 | 1.7 | 1.3 | 0.5 | 2.1 |

TABLE 1-continued

| Intranasal Delivery of DFO (uM in tissues 25 min. after onset of delivery) | | | | | | | | | |
|---|---|---|---|---|---|---|---|---|---|
| Superficial Nodes (4) | 3.4 | 0.9 | 0.6 | 2.2 | 0.6 | 1.8 | 0.6 | 1.1 | 0.8 |
| Cervical Nodes (2) | 12.9 | 10.9 | 34.2 | 58.2 | 51.4 | 65.1 | 13.2 | 11.4 | 8.1 |
| Dorsal Dura | 26.5 | 11.4 | 7.4 | 16.6 | 32.0 | 8.0 | 5.9 | 35.8 | 5.1 |
| Ventral Dura | 25.3 | 38.7 | 70.9 | 58.3 | 44.0 | 51.5 | — | 62.8 | 11.6 |
| Trigeminal Nerve | 33.3 | 14.7 | 22.4 | 72.8 | 25.1 | 26.6 | 17.4 | 27.0 | 9.5 |
| Olfactory Bulbs | 12.7 | 10.6 | 30.0 | 20.5 | 13.1 | 28.0 | 27.5 | 21.6 | 6.6 |
| Anterior Olfactory Nucleus | 4.4 | 4.2 | — | 5.4 | 2.5 | 5.5 | 4.4 | 7.7 | — |
| Frontal Cortex | 4.3 | 3.3 | 13.6 | 2.5 | 1.1 | 6.5 | 1.4 | 5.0 | — |
| Caudate/Putamen | 2.0 | 1.5 | 2.1 | 2.4 | 0.9 | 1.6 | 1.1 | 2.0 | — |
| Septal Nucleus | 2.6 | 1.6 | 1.6 | 3.2 | 1.9 | 2.0 | 1.8 | 2.9 | — |
| Hippocampus | 0.9 | 0.9 | 0.9 | 2.3 | 1.2 | 1.2 | 0.5 | 1.3 | — |
| Parietal cortex | 1.3 | 1.6 | 2.3 | 0.7 | 1.9 | 2.8 | 0.8 | 1.0 | — |
| Thalamus | 1.1 | 1.2 | 1.2 | 1.5 | 1.0 | 1.0 | 0.8 | 1.2 | — |
| Hypothalamus | 5.4 | 7.3 | 6.5 | 3.1 | 3.0 | 6.1 | 2.7 | 3.8 | — |
| Midbrain | 1.3 | 1.3 | 1.1 | 1.8 | 1.3 | 1.2 | 0.6 | 1.3 | — |
| Pons | 2.0 | 1.5 | 1.4 | 1.5 | 2.0 | 2.6 | 0.7 | 2.4 | — |
| Medulla | 1.1 | 2.3 | 1.2 | 1.7 | 2.2 | 3.0 | 1.0 | 2.0 | — |
| Upper Cervical Spinal Cord | 2.1 | 1.4 | 3.7 | 3.9 | 6.8 | 7.3 | 1.4 | 4.6 | 4.6 |
| Cerebellum | 0.8 | 0.9 | 0.6 | 0.9 | 1.4 | 1.1 | 0.5 | 1.1 | — |
| Thyroid | 1125.4 | 2932.7 | 448.2 | 466.7 | 1285.4 | 753.3 | 751.4 | 3463.9 | 605.9 |
| Olfactory Epithelium | 12016.8 | 11374.8 | 11191.7 | 9519.2 | 10724.4 | 11764.8 | 9572.8 | 9321.0 | 12205.2 |
| Axillary Nodes (2) | 0.5 | 0.4 | 0.3 | 0.4 | 0.5 | 0.3 | 0.4 | 1.0 | 3.1 |
| Liver | 0.4 | 0.8 | 0.4 | 0.3 | 0.3 | 0.3 | 0.4 | 0.4 | 0.4 |
| Kidney | 1.0 | 0.4 | 0.5 | 0.4 | 0.2 | 0.6 | 1.0 | 1.2 | 0.5 |
| Muscle | 0.4 | 0.3 | 0.3 | 0.4 | 0.2 | 0.6 | 0.6 | 0.7 | 0.4 |
| Heart | 0.4 | 0.4 | 0.5 | 0.6 | 0.3 | 2.2 | 0.2 | 0.2 | 0.5 |
| Lung | 0.6 | 1.4 | 0.7 | 1.0 | 0.5 | 2.2 | 1.5 | 1.1 | 0.5 |
| Lower Cervical Spinal Cord | 0.5 | 5.3 | 1.0 | 0.3 | 0.1 | 3.8 | 0.4 | 1.8 | 0.3 |
| Thoracic Spinal Cord | 0.1 | 0.2 | 0.2 | 0.1 | 0.1 | 1.2 | 0.3 | 0.6 | 0.1 |
| Lumbar Spinal Cord | 0.1 | 0.1 | 0.1 | 0.1 | 0.7 | 0.1 | 0.1 | 0.1 | 0.1 |
| Spinal Dura | 1.9 | 3.3 | 1.3 | 1.1 | 2.3 | — | 0.4 | 1.5 | 0.8 |

The method of the invention delivers the therapeutic agent to the nasal cavity of a mammal. It is preferred that the agent be delivered to the olfactory area in the upper one-third of the nasal cavity and, particularly, to the olfactory neuroepithelium in order to promote rapid and efficient delivery of the agent to the CNS along the olfactory neural pathway rather than the capillaries within the respiratory epithelium. The preferred transport of the therapeutic agent, e.g., DFO, to the brain by means of the olfactory and trigeminal neural pathways rather than the circulatory system so that the harmful side effects and potentially short half-life of the agent is not an issue. Further, certain agents may simply be unable due to size to cross the blood-brain barrier from the bloodstream into the CNS. The preferred method allows direct delivery of such molecules to the CNS. The data provided in Table 1 above strongly supports the increased efficacy of one embodiment of the inventive method.

To deliver the therapeutic agent to the CNS, the agent alone or in combination with other substances as a pharmaceutical composition may be administered to the olfactory area located in the upper one-third of the nasal cavity. The composition may be administered intranasally as a powdered or liquid spray, nose drops, a gel or ointment, through a tube or catheter, by syringe, packtail, pledget or by submucosal infusion. Optimization of the administration of the therapeutic agent is provided by the various embodiments by applying the agent to the upper third of the nasal cavity.

The optimal concentration of the active therapeutic agent will necessarily depend upon the specific neurologic agent used, the characteristics of the patient and the nature of the disease or condition for which the agent is being used. In addition, the concentration will depend upon whether the agent is being employed in a preventive or treatment capacity. Further, the stage of a particular disease or disorder, e.g., early vs. late Alzheimer's disease, may dictate the optimal concentration of the agent.

Exemplary work performed according to one embodiment of the inventive method was performed, the results of which are illustrated in FIG. 1. The experimental plan included administration of a 10% solution of DFO in distilled water in three doses of 6 mg each (in 60 μl), one dose every three hours, directly to the CNS of laboratory rats via an intranasal (IN) (upper third of naval cavity) route followed by a 2-hour middle cerebral artery occlusion (MCAO) 48 hours post-DFO administration. The animals were sacrificed 5 days after MCAO and the brains removed, sectioned on a brain matrix at 2 mm intervals and then stained with 2,3,5-triphenyltetrazolium chloride (TTC). Infarct volumes were measured using NIH Image.

Intranasal DFO reduced infarct volumes by 60% when expressed as either total infarct, cortical infarct, or striatal infarct volume. Brain proteins from olfactory bulb and from striatum were subjected to Western blot analysis for hypoxia-inducible factor-1α (HIF-1α). See FIG. 1 for a bar graph illustrating the results (10) for control animals (C) and pre-treated animals (P). The results are shown broken into the cortex (12), striatum (14) and overall total (16) infarct volumes for control/pretreated animals. FIG. 1 illustrates the effectiveness of pretreating an animal with IN DFO administration of three doses of 10% DFO to the upper one-third of the nasal cavity (10), using the experimental procedure described above in connection with FIG. 1. Here, the control animals' (C) total infarct volume is 175.93 mm$^3$ (18), while the pretreated animals' (P) total infarct volume is 70.57 mm$^3$ (20). Thus, a reduction of 60% in infarct volume is realized by way of this pretreatment regimen.

Quantitation of the Western blot revealed that the amount of HIF-1α protein present in olfactory bulb and striatum was elevated approximately 30- and 20-fold, respectively. Additional brain samples from animals treated with intranasal DFO were generated, total RNA was isolated from olfactory bulb and striatum, and cDNA was generated using primers specific for HIF-1α. The cDNA was subjected to RT-PCR, and the results suggest that mRNA for HIF-1α was abundant; however, there were no differences in the concentration of HIF-1α mRNA in samples from animals treated with intranasal DFO and their controls treated with intranasal distilled water.

The data thus indicate that intranasal DFO pretreatment protects the brain during stroke via a mechanism involving the transcription factor HIF-1α and that infarct volume is significantly reduced as a result.

Figure 2:
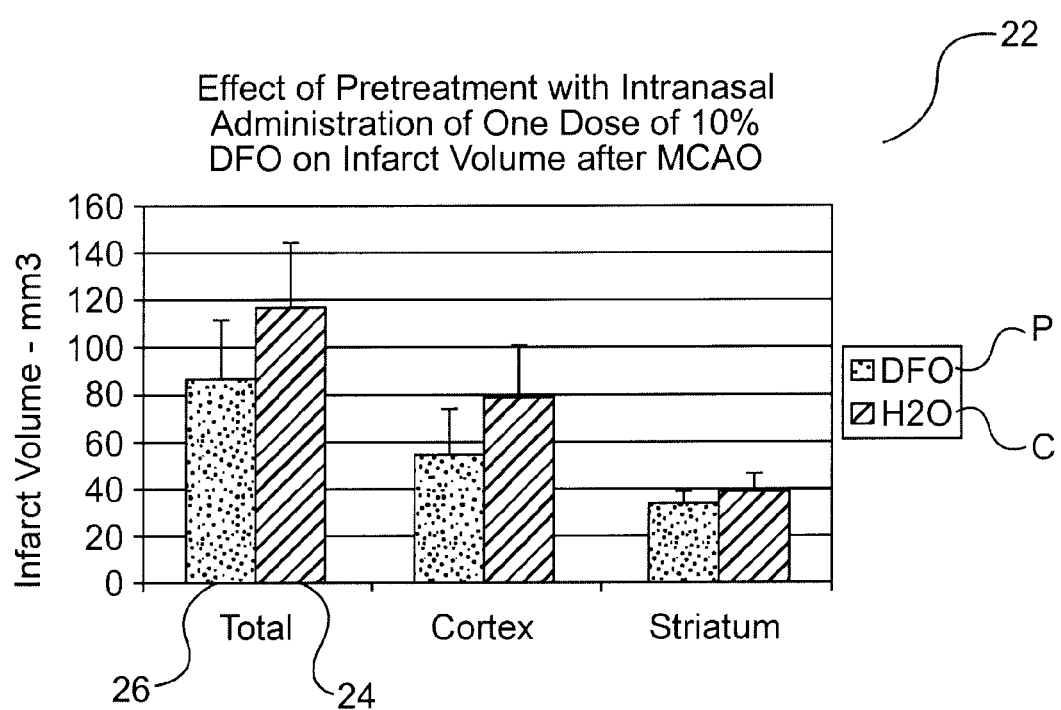
FIG. 2 is a bar graph illustrating pre-stroke treatment with intranasal administration of one dose of 10% DFO and its effect on infarct volume.

With reference to FIG. 2, data indicating the effectiveness of pretreating an animal with IN DFO administration of one dose of 10% DFO to the upper one-third of the nasal cavity (22), using the experimental procedure described above is illustrated. As illustrated, the total infarct volume is reduced 5 days after MCAO as discussed above, as compared with controls treated with distilled water. The control animals' (C) total infarct volume is measured at 117.28 mm$^3$ (24), while the pretreated animals' (P) infarct volume is 86.72 mm$^3$ (26), an overall infarct volume reduction of 26%.

Figure 3:
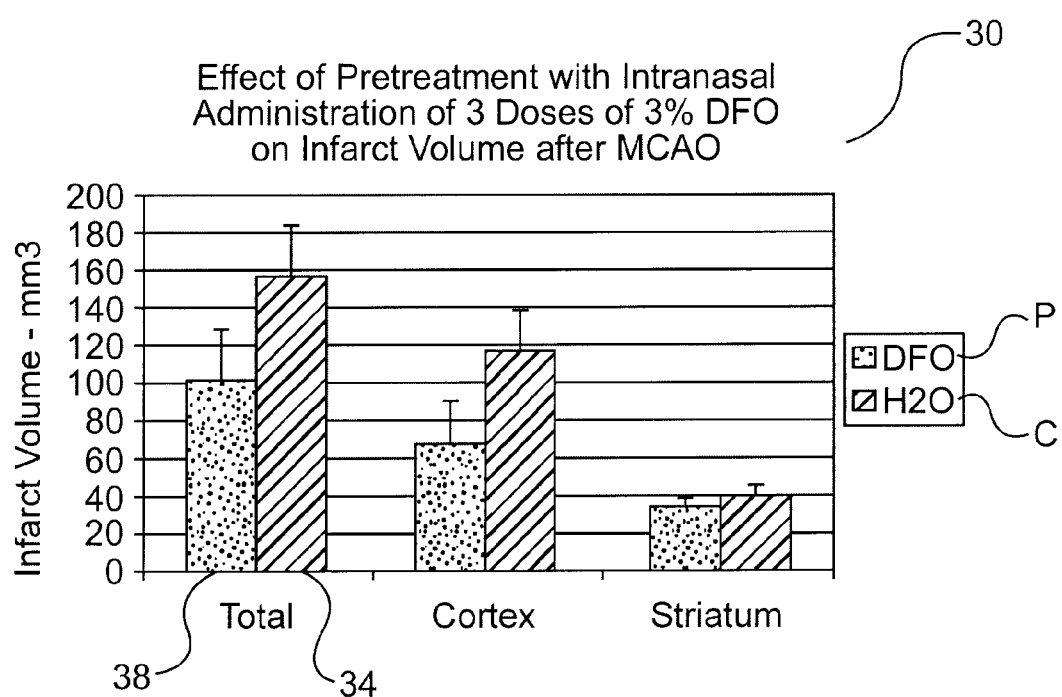
FIG. 3 is a bar graph illustrating pre-stroke treatment with intranasal administration of three doses of 3% DFO and its effect on infarct volume.

Referring now to FIG. 3, data indicating the effectiveness of pretreating an animal with IN DFO administration of three doses of 3% DFO to the upper one-third of the nasal cavity, using the experimental procedure described above is illustrated (30). Here, the control animals' (C) total infarct volume is 157.01 mm$^3$ (34), while the pretreated animals' (P) total infarct volume is measured to be 101.83 mm$^3$ (38), a reduction of 35%.

As the data presented in FIGS. 1-3 indicate, preconditioning animals by administering IN DFO, or other metal chelator, to the upper one-third of the nasal cavity significantly reduces total infarct volume. The Figures further indicate significant reduction of infarct volumes located in the Cortex and Striatum.

Thus, in one embodiment of the invention, an effective amount or dose of a metal chelator, e.g., DFO, deferasirox or deferiprone, may be administered intranasally to precondition the CNS to protect a mammal against the potential of cerebral ischemia resulting from, e.g., coronary artery bypass graft (CABG) surgery. The administration of an effective amount of a metal chelator in the upper one-third of the nasal cavity eliminates the unwanted and potentially lethal side effects of DFO, for example, possible shock and rapid elimination, while providing the agent with virtually instant access to the CNS. Other metal chelating agents may have similar unwanted systemic effects. The metal chelator acts to increase the HIF-1α subunit concentration and stability of the HIF-1α subunits in the CNS. In this manner, the metal chelator performs to condition, or precondition, the CNS in anticipation of possible cerebral ischemia resulting from the CABG surgery; establishing a neuroprotective state against a future episode of cerebral ischemia.

Several neurologic disorders as defined herein may be prevented, or the effects minimized, using different embodiments of the inventive method. For example, patients at risk for Alzheimer's disease may be aided by the technique, as this disease involves neurodegeneration, preceded by cerebral vascular difficulties. See, e.g., The Lancet Neurology, vol. 3, pp. 184-190, Jack C. de la Torre (March, 2004). Thus, patients at risk for Alzheimer's disease may be pretreated using one or more of the inventive embodiments disclosed herein.

Further, in another embodiment, those patients scheduled for coronary artery bypass graft (CABG) surgery may also benefit due to the relatively high percentage of post-surgical cerebral ischemia.

In another embodiment, patients at risk for Parkinson's disease may benefit from the inventive method.

In yet another embodiment, patients at risk for stroke may be aided by the inventive method. Such patients would include those having risk factors comprising hypertension, diabetes, obesity, smoking, antiphospholipid syndrome or with a history of stroke (thus prone to subsequent stroke).

The above embodiments essentially focus on prevention of the cognitive, behavioral and physical impairment due to cerebral ischemia as a result of certain episodes, disorders or medical procedures by pretreatment using IN administration of a metal chelator, e.g., DFO or deferasirox, to the upper one-third of the nasal cavities. A series of alternate embodiments focus on treating and/or minimizing the effects of such disorders after they have been diagnosed.

Figure 4:
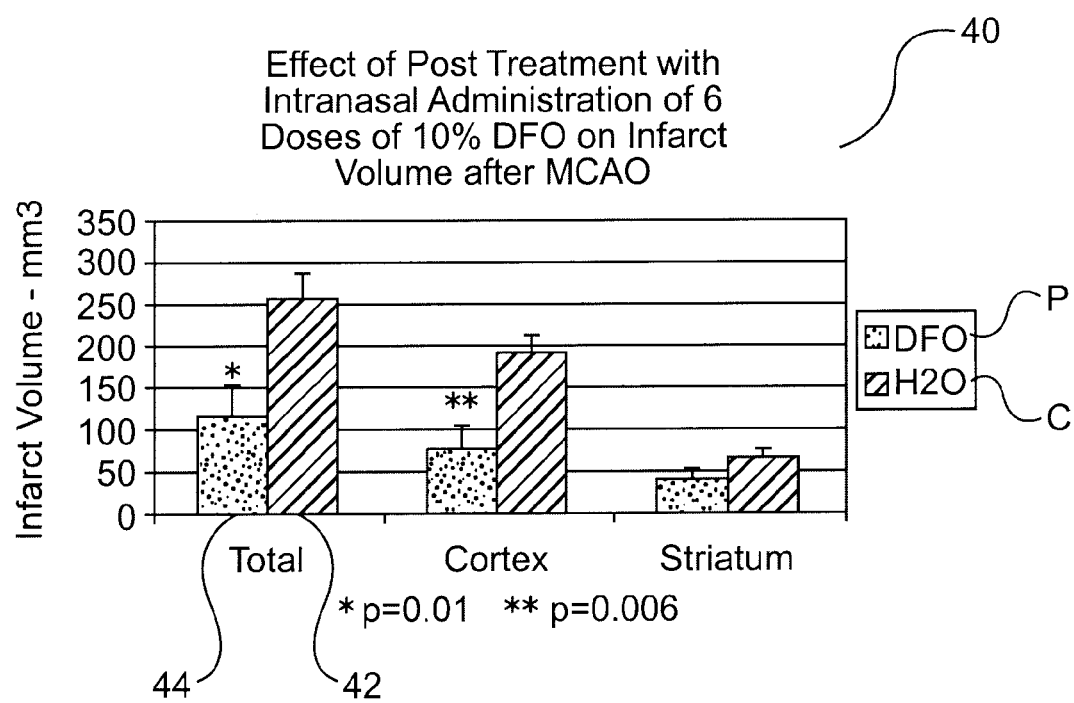
FIG. 4 is a bar graph illustrating post-stroke treatment with intranasal administration of six doses of 10% DFO and its effect on infarct volume.

In this regard, let us now turn to FIG. 4. Here, the experimental method is as follows: The method is the same as described above in connection with FIG. 1, except that the subjects are not pretreated. Instead, IN DFO is administered to the upper one-third of the nasal cavity at the start of reperfusion to treat the subjects. Six doses of 10% DFO (6 mg DFO/dose) were administered in this manner; three doses of 10% DFO at 2-hour intervals on the day of surgery and the remaining three doses of 10% DFO at three-hour intervals on the day following surgery (40). Examination of the patient brains reveals that the total infarct volume was 257 mm$^3$ (42) in the control animals (C) (treated with distilled water) and 116 mm$^3$ (44) in animals pretreated with IN DFO(P); a reduction of 55%.

Thus, for example, one embodiment of the inventive method may be used to treat a patient having, or recently having undergone, a stroke.

In another embodiment, the inventive method may be used in a treatment plan for patients at risk for, or diagnosed with, Alzheimer's disease.

In another embodiment, the inventive method may be used to treat patients at risk for, or diagnosed with, Parkinson's disease.

In another embodiment, the inventive method may be used to treat patients at risk for, or diagnosed with, Wilson's disease.

In still another embodiment, the inventive method may be used to treat patients at risk for, or diagnosed with, Huntington's disease.

In another embodiment, the inventive method may be used to treat patients at risk for, or diagnosed with, traumatic brain injury, spinal cord injury, iron overload, or cerebral hemorrhage.

In yet another embodiment, patients at risk for, or diagnosed with, stroke and/or transient ischemic attack, and thus at risk for a subsequent stroke, may benefit from the inventive method.

Further, another experiment was conducted to further discover the mechanisms that may be manipulated in order to achieve the desired therapeutic results. Thus, rats were treated with 3 doses of 60 μl 10% intranasal deferoxamine (DFO), or water, at 3 hours intervals. The two groups of rats were either sacrificed or subjected to a 2-hour Middle Cerebral Artery Occlusion (MCAO) 48 hours later. Those rats undergoing the MCAO were sacrificed 24 hours after the MCAO.

The extracted and purified RNA from the two groups of rats was subjected to gene chip expression analysis performed using the Amersham CodeLink™ Gene Expression Bioarray System supplied by GE Healthcare, according to the technical manual. Gene expression was assessed by hybridization to CodeLink™ whole rat genome (35K) gene chips.

The data obtained from the bioarray system was checked for quality and normalized to median background of the slide using the CodeLink™ analysis software. The data was then analyzed for changes (up-regulation, down-regulation) in gene expression using the GeneSifter® software, a product of VizX Labs, located at 200 West Mercer Street, Suite 500, Seattle, Wash.

Gene expression was assessed by hybridization to CodeLink™ whole rat genome (35K) gene chips, 24 hours after MCAO (stroke) in a group of non-DFO-pretreated rats as well as in a group of rats pretreated 48 hours prior to MCAO with intranasal DFO according to the present invention as described above. The general pattern of gene expression in both cases indicates a differential expression of genes in stroke but not following DFO treatment (without stroke) as well as in pre-treated DFO rats vs untreated rats following stroke. Gene expression was then verified by PCR for select genes as further discussed below.

In addition to the bioarray and PCR results, total infarct volume, cortical infarct volume and brain swelling was assessed for the rats pretreated with intranasal DFO with stroke and untreated rats with stroke 24 hours after MCAO. The data indicates a 56% decrease in total infarct volume, a 72% decrease in cortical infarct volume and a 71% decrease in brain swelling. Thus, the results indicate that pretreatment or preconditioning as described above with intranasal DFO prior to stroke decreases total infarct volume, cortical infarct volume and brain swelling occurring as a result of stroke.

Figure 5:
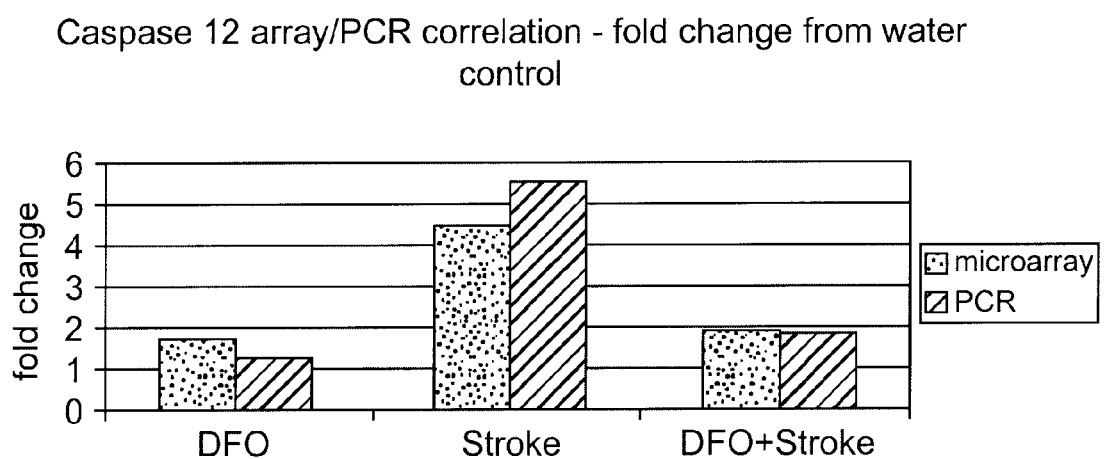
FIG. 5 is a bar graph illustrating the differential reduction, prevention or inhibition of the expression of caspase-12 by intranasal DFO.

The PCR results for caspase-12 are provided in FIG. 5. Expression of the gene for caspase-12 is increased in ischemic conditions. Caspase-12 is involved in apoptosis and cell death mechanisms and its expression is increased in the neurological disorders defined herein. Therefore, differential prevention, reduction or inhibition of the increased expression of the gene for caspase-12 will help prevent and/or treat apoptosis and/or cell death. Thus, apoptosis and cell death involved in the neurological disorders defined herein may be prevented and/or treated by differentially preventing, reducing or inhibiting the increase of expression of the gene for caspase-12.

FIG. 5 indicates that an intranasally administered metal chelator, e.g., DFO, differentially prevents, reduces or inhibits the increase in caspase-12 caused by the ischemic conditions induced by stroke.

Figure 6:
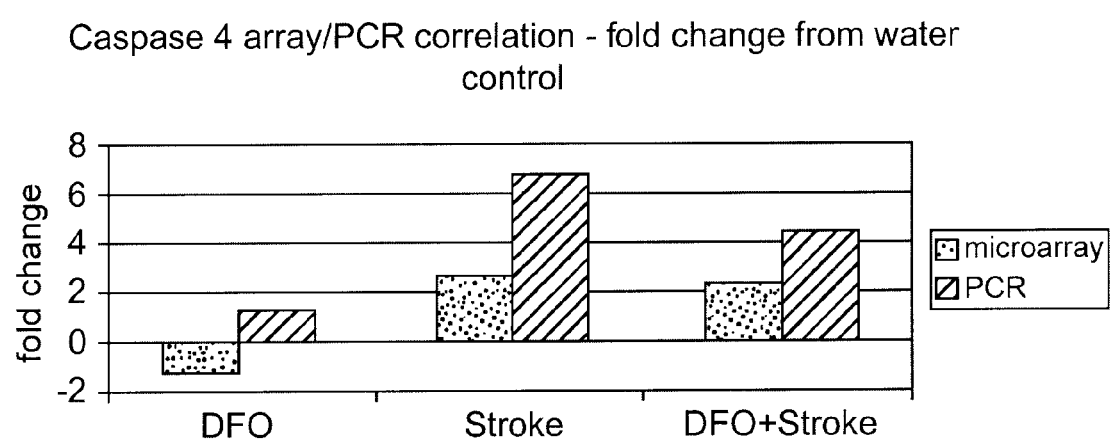
FIG. 6 is a bar graph illustrating the differential reduction, prevention or inhibition of the expression of caspase-4 by intranasal DFO.

FIG. 6 illustrates the PCR results for caspase-4. The results indicate that an intranasally administered metal chelator, e.g., DFO, differentially prevents, inhibits or reduces the increase in caspase-4 caused by the ischemic conditions induced by stroke. Increased expression of caspase-4 is associated with the terminal stages of apoptosis and inflammation and is caused by the neurological disorders defined herein. Thus, apoptosis and/or inflammation involved in the neurological disorders defined herein may be prevented and/or treated by differentially preventing, reducing or inhibiting the increase of expression of the gene for caspase-4 with an intranasal metal chelator such as DFO.

Figure 7:
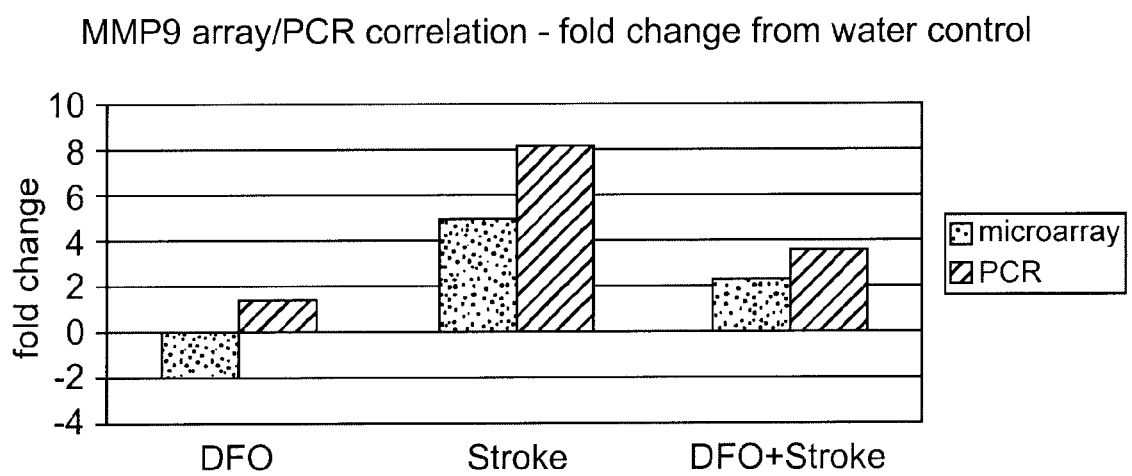
FIG. 7 is a bar graph illustrating the differential reduction, prevention or inhibition of the expression of matrix metallopeptidase 9 (MMP9) by intranasal DFO.

FIG. 7 illustrates the marked differential reduction, inhibition or prevention of the increased expression of the gene for the matrix metallopeptidase-9 (MMP9). Expression of the gene for MMP9 is increased in ischemic conditions such as stroke and is involved in apoptosis, brain swelling, and cellular damage following stroke and has been linked to an increased risk for hemorrhagic transformation following ischemic conditions. Thus, an intranasally administered metal chelator according to the present invention, e.g., DFO, reduces, inhibits or prevents the increase in the expression of the gene for MMP9 caused by the neurological disorders defined herein and, therefore, may be used to prevent and/or treat the neurologic disorders.

Figure 8:
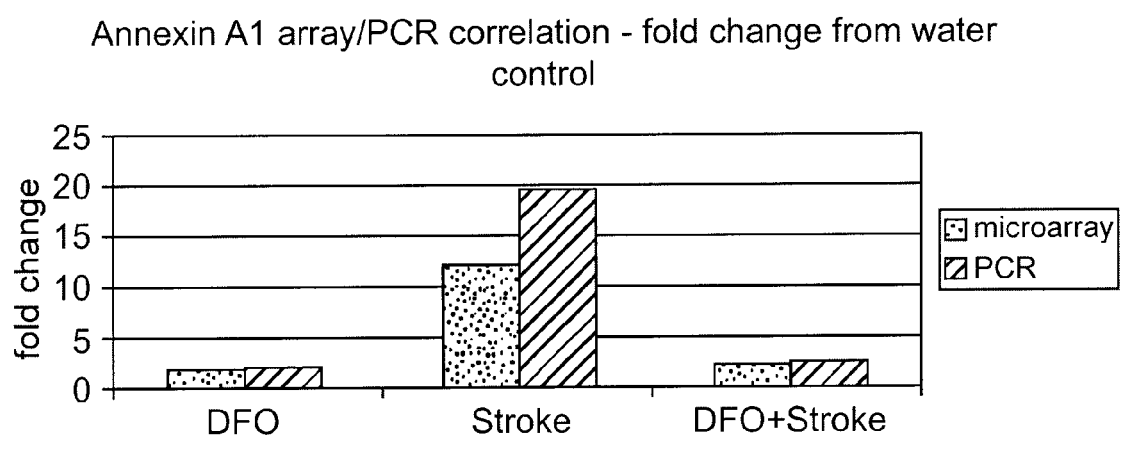
FIG. 8 is a bar graph illustrating the differential reduction, prevention or inhibition of the expression of annexin-A1 by intranasal DFO.

FIG. 8 illustrates PCR verification data for the gene for annexin-A1. Annexin-A1 gene expression is increased in ischemic conditions such as stroke, increasing in response to inflammation. The data indicates that intranasally administered metal chelator according to the present invention, e.g., DFO, greatly reduces brain inflammation. Therefore, the present invention may be used to differentially reduce, inhibit and/or prevent the increase in the expression of the gene for annexin-A1 caused by a neurological disorder by reducing brain inflammation. In turn, the present invention may be used to prevent and/or treat the neurological disorders as defined herein.

Figure 9:
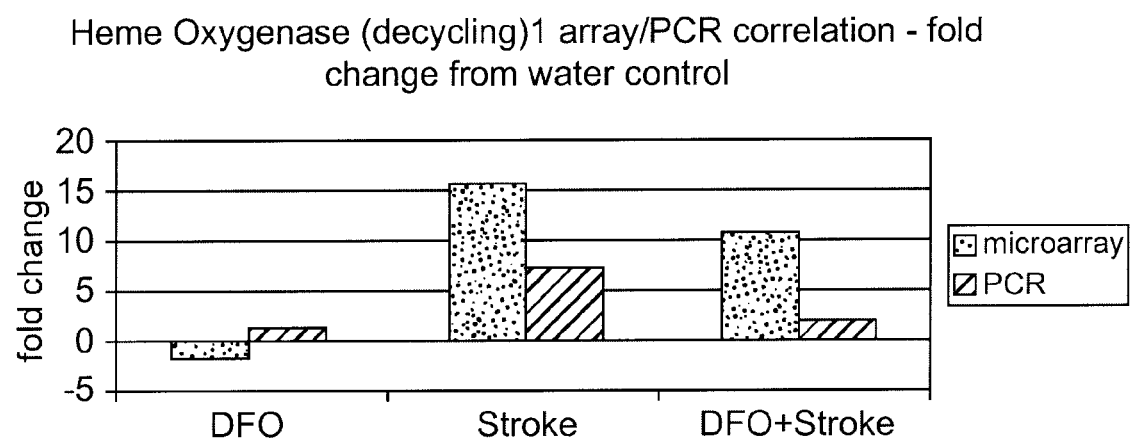
FIG. 9 is a bar graph illustrating the differential reduction, prevention or inhibition of the expression of heme oxygenase (decycling)-1 by intranasal DFO.

FIG. 9 provides PCR data that indicates that the intransal administration of a metal chelator, e.g., DFO, of the present invention greatly reduces the increase in heme oxygenase (decycling)-1 caused by ischemic conditions such as stroke. Heme oxygenase (decycling)-1 and heme oxygenase-1 are used interchangeably herein as is known to those skilled in the art, each representation of the compound being within the scope of the present invention. The gene for heme oxygenase (decycling)-1 is increased in response to oxidative stress in ischemic conditions such as stroke and Alzheimer's disease, as well as the neurological disorders defined herein. As a result, the present invention may be used to differentially reduce, inhibit, or prevent the increased expression of the gene for heme oxygenase (decycling)-1 caused by the defined neurological disorders and, in turn, to prevent and/or treat the neurological disorders.

Figure 10:
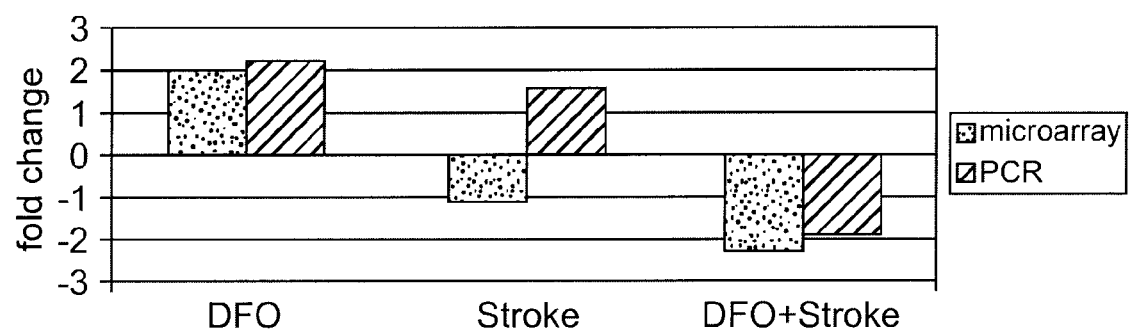
FIG. 10 is a bar graph illustrating the differential reduction, prevention or inhibition of the expression of insulin-like growth factor-2 (IGF-2) following stroke by intranasal DFO.

FIG. 10 provides PCR results for insulin-like growth factor 2 (IGF-2). The expression of the gene for IGF-2 is increased in ischemic conditions such as stroke and the other neurological disorders defined herein. IGF-2 administered intracerebroventricularly following hypoxia/ischemia has been shown to increase neuronal loss in the hippocampus and dentate gyrus and even blocks the neuroprotective effects of IGF-1. IGF-2 may antagonize the protective effect of IGF-1 by displacing it from IGF binding proteins or from its receptor. The data indicates that intransally administering a metal chelator, e.g., DFO, according to the present invention significantly reduces the increased expression of IGF-2 following stroke. Therefore, the intransally administering a metal chelator, e.g., DFO may be used to differentially reduce, inhibit or prevent the increased expression of IGF-2 caused by a neurological disorder and, as a result, to prevent and/or treat the neurological disorder.

In another embodiment of the present invention, memory loss may be prevented or treated and memory improved in patients with Alzheimer's disease. In an experiment under the present invention, Alzheimer's transgenic mice (APP/PS1) were treated with intranasally administered deferoxamine (DFO), a metal chelator, for four months and compared with Alzheimer's mice treated intranasally with a PBS solution and a set of control mice treated intransally with a PBS solution. The three treatment groups were intranasally treated every Monday, Wednesday, and Friday for four months beginning at 36 weeks of age. The three treatment groups were tested in a Morris Water Maze before the beginning of treatment and again every month over the four months of treatment. The average path length and average escape latency were calculated for each treatment group at each test point.

Figure 11:
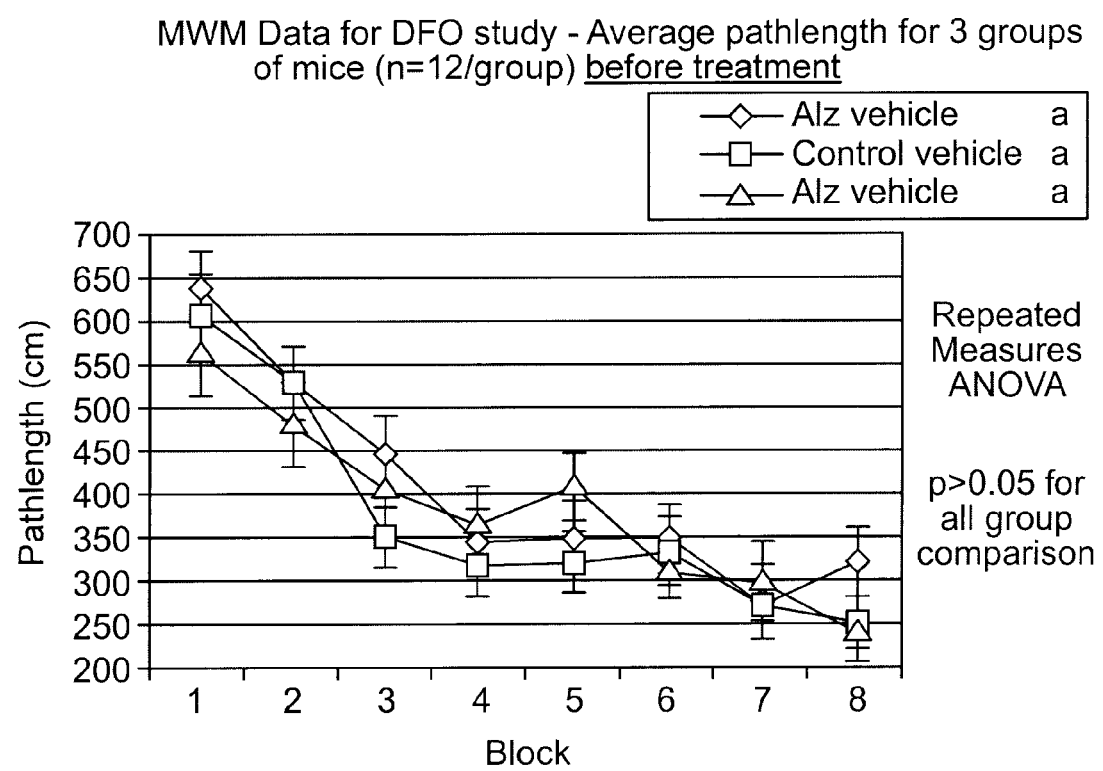
FIG. 11 is a graph illustrating baseline comparison of three treatment groups in average Morris water maze path length.
Figure 12A:
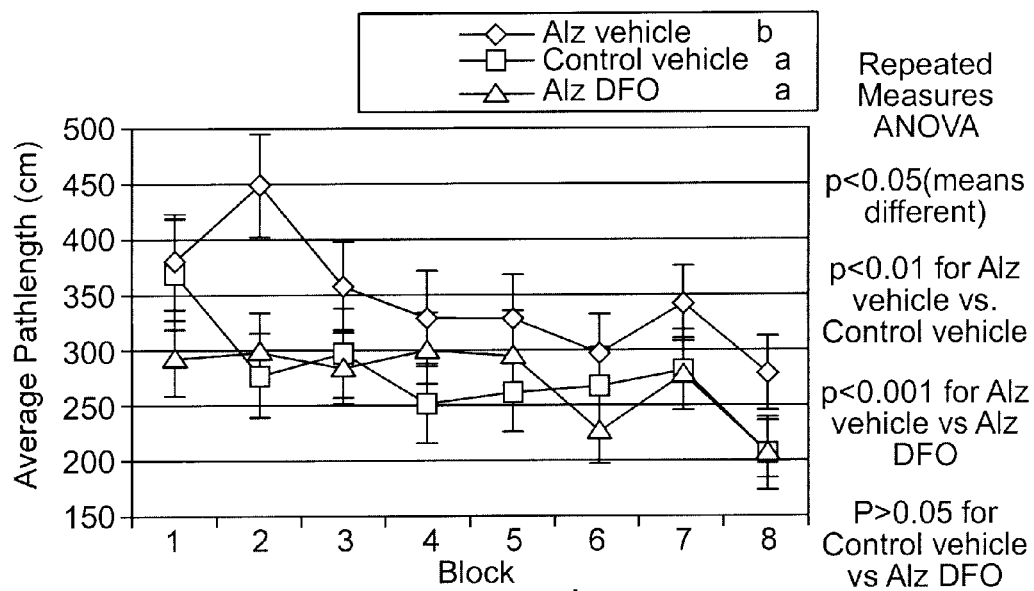
FIG. 12A illustrates comparison of average path length in the Morris water maze for three treatment groups after two months of treatment.
Figure 12B:
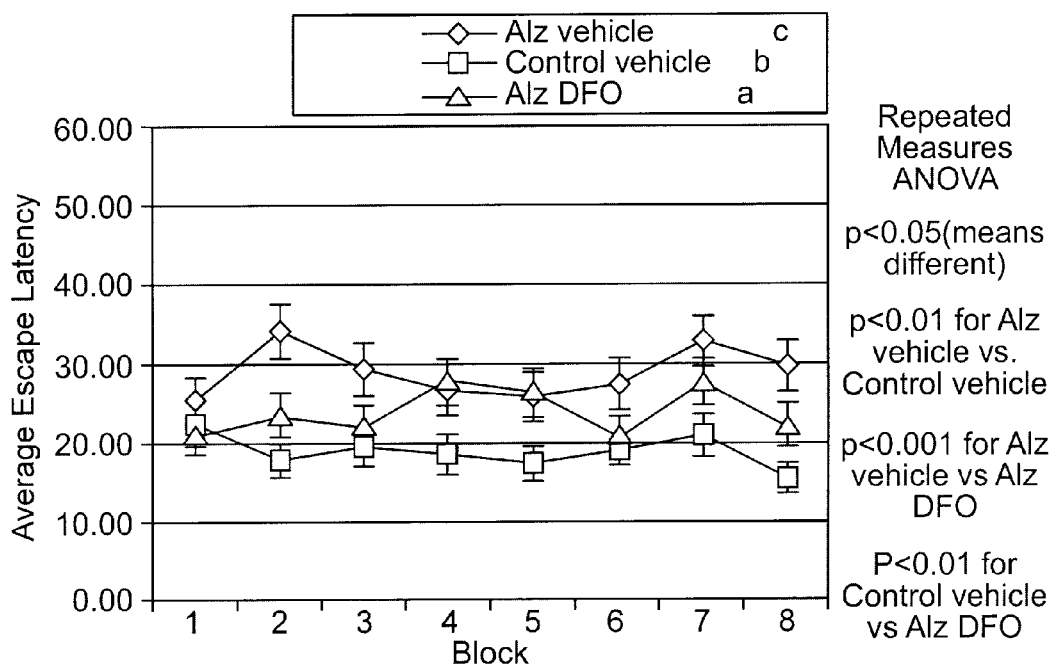
FIG. 12B illustrates comparison of average escape latency from the Morris water maze for three treatment groups after two months of treatment.

Turning now to FIG. 11, the data indicates no significant difference between the treatment groups at baseline in terms of average path length. As indicated in FIG. 12A, at the two month test point, the control group and the Alzheimer-DFO treated group were statistically indistinguishable in terms of path length but both groups were significantly shorter than the Alzheimer-PBS treated group. FIG. 12B indicates a statistically significant difference in escape latency among the three treatment groups, with the Alzheimer-PBS group taking longest to escape, the Alzheimer-DFO group taking less time and the control group taking the shortest time to escape the maze.

Figure 13A:
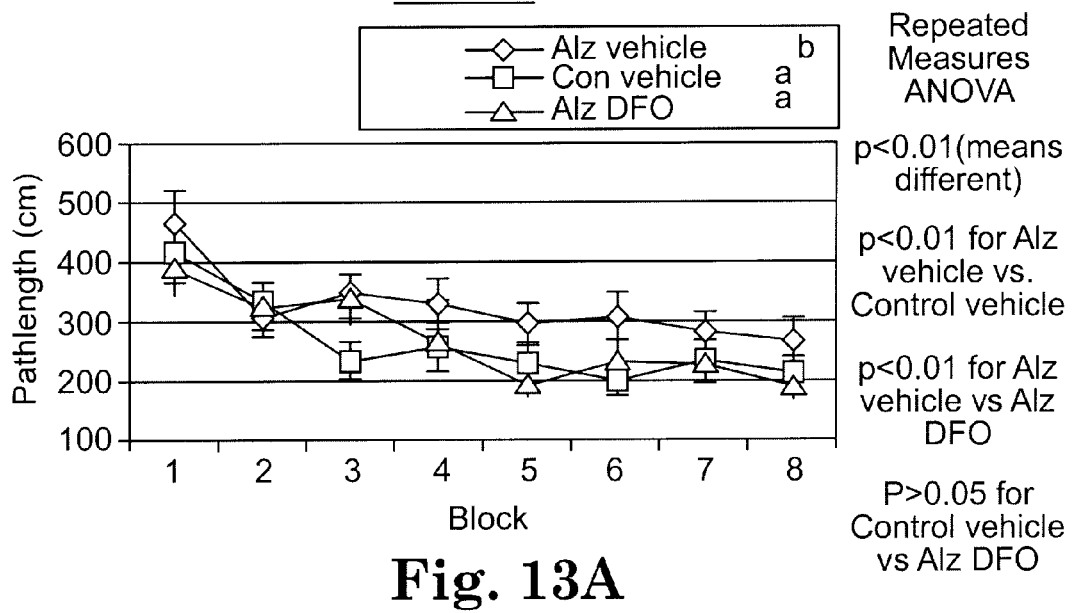
FIG. 13A illustrates comparison of average path length in the Morris water maze for three treatment groups after four months of treatment.
Figure 13B:
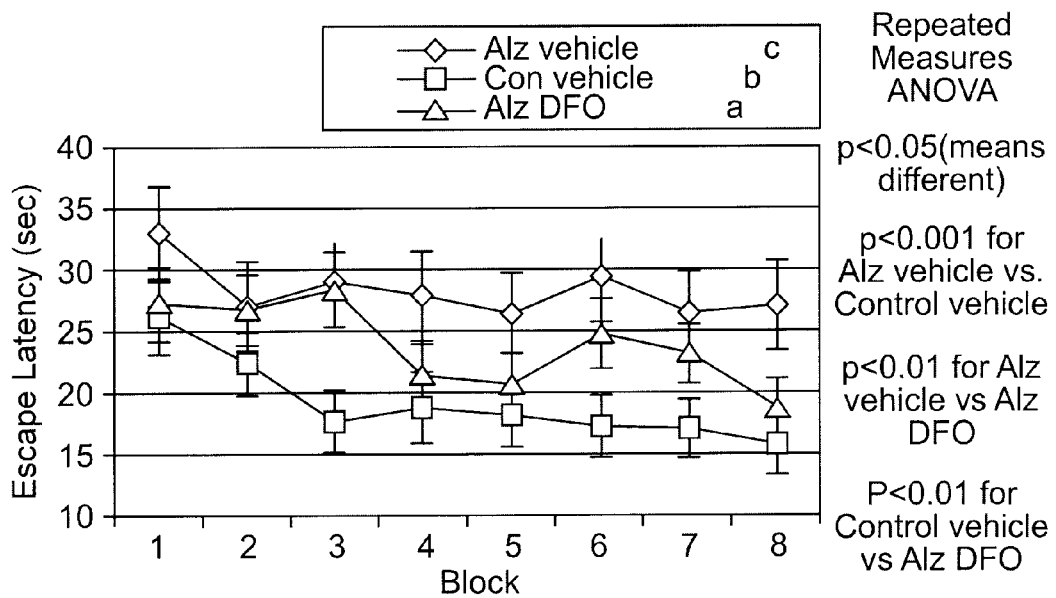
FIG. 13B illustrates comparison of average escape latency from the Morris water maze for three treatment groups after four months of treatment.

Similarly, as indicated in FIG. 13A, at the four month time point, the control group and the Alzheimer-DFO group were statistically indistinguishable in terms of average path length. Both groups had significantly shorter average path lengths than the Alzheimer-PBS group. Moreover, after four months of treatment, as illustrated in FIG. 13B, a statistically significant difference in escape latency was observed, with the same hierarchy of latency as observed at two months, i.e., the Alzheimer-PBS group had the longest escape latency, the Alzheimer-DFO group had a shorter latency and the control group had the shortest latency.

The results indicate that DFO-treated Alzheimer's mice performed significantly better than non-treated Alzheimer's mice in a standard test of spatial memory after only two months of treatment. Therefore, intranasal DFO protects against and significantly reduces memory loss, i.e., improves memory loss, occurring as a consequence of Alzheimer's disease.

Accordingly, intranasal administration of metal chelators according to the present invention, e.g., DFO, deferasirox, may be used to prevent and treat memory loss and neuronal loss as a result of iron accumulation in the central nervous system, aging, neurodegeneration, mild cognitive impairment, Alzheimer's disease, stroke, Parkinson's disease, Lewy body dementia, progressive supranuclear palsy, amyotrophic lateral sclerosis, metal poisoning, and iron overload.

DFO, deferasirox and deferiprone are particular examples of metal (iron) chelators that may be used in one embodiment to stimulate and/or stabilize HIF-1α to achieve the desired neuroprotective result. Other iron chelators that may be administered according to an embodiment of the method comprise compounds from the hydroxamate family, and salicylaldehyde isonicotinoyl hydrazone. Other equivalent iron chelating compounds will present themselves readily to those skilled in the art and are within the scope of the disclosure.

Alternatively, copper chelating compounds may be administered according to an embodiment of the method and comprise trientine, clioquinol, n-acetyl cysteine amide, tetrathiomolybdate and bi-pyridyl compounds. Other equivalent copper chelating compounds will present themselves readily to those skilled in the art and are within the scope of the disclosure.

In another embodiment, a pharmaceutical composition may be comprised of a combination of at least one metal chelating compound to achieve the results of the various embodiments of the inventive method described above. Another pharmaceutical composition of the present invention may comprise a combination of at least one copper-chelating compound. Yet another embodiment of a pharmaceutical composition according to the inventive method may comprise a combination of at least one iron-chelating compound coupled with at least one copper-chelating compound.

In still another embodiment, a pharmaceutical composition of the present invention may be comprised of a combination of at least one metal-chelating compound with at least one antioxidant such as vitamin E, myricetin, curumin, catechin and/or lycopene.

One embodiment of the pharmaceutical composition of the present invention is effective to prevent and treat the animal central nervous system impairment of cognitive, behavioral and physical function due to cerebral ischemia, neurodegeneration, trauma to the central nervous system caused by a neurological disorder as defined herein. In this embodiment, the pharmaceutical composition may comprise a therapeutic agent comprised of at least one dose of an iron chelator, a copper chelator and an antioxidant, effective to differentially inhibit, reduce or prevent the increased expression of genes selected from the group consisting of caspase-12, caspase-4, matrix metallopeptidase-9 (MMP9), annexin-A1, heme oxygenaase (decycling)-1, and insulin-like growth factor-2 (IGF-2). In this embodiment, the increased expression of the at least one gene is caused by the neurological disorder. Moreover, in this embodiment, the pharmaceutical composition may be administered intranasally to the upper one-third of the patient's nasal cavity prior to and/or after the impairment of the animal central nervous system.

In another embodiment of the present invention, a pharmaceutical composition comprised of DFO, deferasirox or deferiprone, IGF-1, trientine, clioquinol, n-acetyl cysteine amide, tetrathiomolybdate and/or bi-pyridyl compounds may be administered.

In general, any of the therapeutic agents or pharmaceutical compositions described or referenced herein may be administered to patients or subjects under embodiments of the inventive method prior to a surgical procedure such as CABG, during such a procedure or after such a procedure.

Preferentially, the inventive method, and embodiments thereof, focuses on chelating iron and/or copper. This chelation strategy thus prevents cycling of iron and/or copper between an oxidized and a reduced state. Such cycling is highly undesirable as free radicals are formed. Free radicals and other reactive oxygen species, e.g., $H_2O_2$, HOCl and radicals such as $O_2^-$, sulfur cation, nitric oxide radical, ferryl, peroxyl, peroxynitrite, thiyl, thiylperoxyl and alkoxyl, are highly reactive and may be highly damaging to cellular components as the free radicals react. Free radical reactions may crosslink proteins, mutate DNA and peroxidize lipids. Such reactions have deleterious effects on cellular homeostasis. Thus, controlling the iron and copper ions through chelating agents reduces or eliminates such free radical damage from the oxidation/reduction cycling.

As a result, virtually any compound that prevents the cycling of iron and copper between the oxidized and reduced state may be used in different embodiments of the inventive method.

In still another embodiment, the therapeutic agent according to the inventive methods may comprise one or more of the following substances which stimulate and/or stabilize HIF-1α: insulin, IGF-I, heregulin insulin, heregulin, TGFbeta, IL-1 beta, TNFalpha, cobalt, pyruvate, oxalacetate and lactate. It is within the scope of invention to create a pharmaceutical composition combining one or more of the foregoing substances. In addition, in other embodiments, the invention may administer a pharmaceutical composition comprising at least one of the foregoing substances with at least one metal chelator. Further, a pharmaceutical composition may be comprised in another embodiment of at least one of the foregoing substances combined with at least one antioxidant such as vitamin E, myricetin, curumin, catechin and/or lycopene.

An effective amount, as herein defined, of the therapeutic agent to be administered pursuant to embodiments of the invention is the most preferred method of expression of dosage. Such effective amount is dependent upon many factors, including but not limited to, the type of disease or condition giving rise to an anticipated cerebral ischemic episode, the patient's general health, size, age, and the nature of treatment, i.e., short-term of chronic treatment. For illustrative purposes only, exemplary treatment regimens relating generally to the therapeutic agents disclosed herein, including dosage ranges, volumes and frequency are provided below:

Efficacious dosage range: 0.0001-1.0 mg/kg.

A more preferred dosage range may be 0.005-1.0 mg/kg.

The most preferred dosage range may be 0.05-1.0 mg/kg.

The dosage volume (applicable to nasal sprays or drops) range may be 0.015 ml-1.0 ml.

The preferred dosage volume (applicable to nasal sprays or drops) range may be 0.03 ml-0.6 ml.

Generally, the treatment may be given in a single dose or multiple administrations, i.e., once, twice, three or more times daily over a period of time. For chronic disorders such as those diagnosed with, or at risk for, Alzheimer's disease, stroke or Parkinson's disease, the treatment may consist of at least one dose per day over an extended period of time. Alternatively, for those patients anticipating CABG surgery, the treatment may be a one-time dose to precondition the CNS in anticipation of potential cerebral ischemia. Such preconditioning may require more than one dose and may be administered from 12 hours to 1 week prior to the CABG surgery. Post-stroke treatment may require more than one dose which may be administered several times over the course of a day, wherein this treatment regimen may encompass a week or more.

The brain concentrations that are likely to be achieved with the dosage ranges provided above are, for a single dose: 0.1 nM-50 μM. Over the course of a multi-dose treatment plan, the maximum brain concentration may be as high as 500 μM.

The present invention should not be considered limited to the particular examples described above, but rather should be understood to cover all aspects of the invention. Various modifications, equivalent processes, as well as numerous structures to which the present invention may be applicable will be readily apparent to those of skill in the art to which the present invention is directed upon review of the present specification.

What is claimed is:

1. A pharmaceutical composition for treatment of a neurological disorder comprising increased expression of at least one of the following genes in mammals: caspase-12, caspase-4, matrix metallopeptidase-9 (MMP9), and heme oxygenase (decycling)-1, the composition comprising:
   an effective amount of deferoxamine;
   an effective amount of at least one antioxidant, and
   an effective amount of insulin,
   wherein the pharmaceutical composition comprises a volume of 0.03 ml to 0.6 ml,
   the pharmaceutical composition being in a form that can be administered to the upper third of a mammal's nasal cavity and effective in prevention and/or inhibition of the increased gene expression in mammals while stimulating expression of HIF-1α.

2. The pharmaceutical composition of claim 1, further comprising the at least one antioxidant selected from the group consisting of myricetin, vitamin E, curcumin, catechin, and lycopene.

3. The pharmaceutical composition of claim 1, wherein the administered pharmaceutical composition inhibits development of memory loss in the patient.

4. The pharmaceutical composition of claim 1, wherein the administered pharmaceutical composition inhibits development of spatial memory loss in the patient.

5. The pharmaceutical composition of claim 1, wherein the effective dose of DFO is 0.005 to 1.0 mg/kg.

6. The pharmaceutical composition of claim 1, wherein the neurological disorder comprises Alzheimer's disease.

7. The pharmaceutical composition of claim 1, wherein the neurological disorder is selected from the group consisting of: amyotrophic lateral sclerosis, ischemia, neurodegeneration, Huntington's disease, Parkinson's disease, iron overload within the brain, and traumatic brain injury.

8. A method for treating a patient with a neurological disorder consisting of increased expression of at least one of the following genes in mammals: caspase-12, caspase-4, matrix metallopeptidase-9 (MMP9), and heme oxygenase (decycling)-1, comprising:
   providing at least an effective amount of the composition of claim 1;
   administering the at least an effective amount of the composition intranasally to the upper third of the patient's nasal cavity, thereby enabling the administered composition to bypass the patient's blood-brain barrier and delivering an effective amount of the composition to the patient's brain;
   reducing the expression of the at least one gene; and
   treating the neurological disorder, wherein the neurological disorder is selected from the group consisting of Alzheimer's disease, amyotrophic lateral sclerosis, ischemia, neurodegeneration, Huntington's disease, Parkinson's disease, iron overload within the brain, and traumatic brain injury.

* * * * *